United States Patent
Hamlin et al.

(10) Patent No.: US 6,327,496 B1
(45) Date of Patent: Dec. 4, 2001

(54) IONTOPHORESIS ELECTRODE

(75) Inventors: Robert Hamlin, Stillwater; Robert Clapp, Bloomington; Robert E. Burgmeier, Plymouth, all of MN (US)

(73) Assignee: EMPI Corp., St. Paul, MN (US)

( * ) Notice: Subject to any disclaimer, the term of this patent is extended or adjusted under 35 U.S.C. 154(b) by 0 days.

(21) Appl. No.: 09/351,782

(22) Filed: Jul. 12, 1999

(51) Int. Cl.$^7$ ................................................ A61N 14/30
(52) U.S. Cl. .............................................. 604/20; 604/501
(58) Field of Search ....................... 604/20, 500, 501, 604/890.1, 892.1, 304, 305, 306, 307, 308

(56) References Cited

U.S. PATENT DOCUMENTS

| | | | |
|---|---|---|---|
| 4,886,489 | 12/1989 | Jacobsen et al. | 604/20 |
| 4,973,303 | 11/1990 | Johnson et al. | 604/20 |
| 5,057,072 | 10/1991 | Phipps | 604/20 |
| 5,084,008 | 1/1992 | Phipps | 604/20 |
| 5,380,272 | 1/1995 | Gross | 604/20 |
| 5,431,625 | 7/1995 | Fabian et al. | 604/20 |
| 5,450,845 | 9/1995 | Axelgaard | 128/640 |
| 5,511,548 | 4/1996 | Riazzi et al. | 128/641 |
| 5,620,580 | 4/1997 | Okabe et al. | 204/550 |
| 5,785,040 | 7/1998 | Axelgaard | 128/640 |
| 5,840,056 | 11/1998 | Atanasoska | 604/20 |

*Primary Examiner*—Manuel Mendez
(74) *Attorney, Agent, or Firm*—Oppenheimer Wolff & Donnelly LLP

(57) ABSTRACT

An iontophoresis electrode (10) is disclosed including a backing layer (22) formed of PVC or similar material including plasticizers providing softness and conformability and a conductive layer (18) formed of carbon or similar polymer material having electrical characteristics which are negatively affected with the migration of the plasticizers. A barrier layer (26) is provided to prevent the undesired migration of plasticizers from the backing layer (22) into the conductive layer (18). In one preferred form, the barrier layer (26) is a sacrificial layer, such as of identical construction as the conductive layer (18), for acceptance of the migration of the plasticizers. In another form, the barrier layer (26) is an impermeable layer formed of material in which the plasticizer is immiscible so as to prevent the migration of the plasticizers.

20 Claims, 1 Drawing Sheet

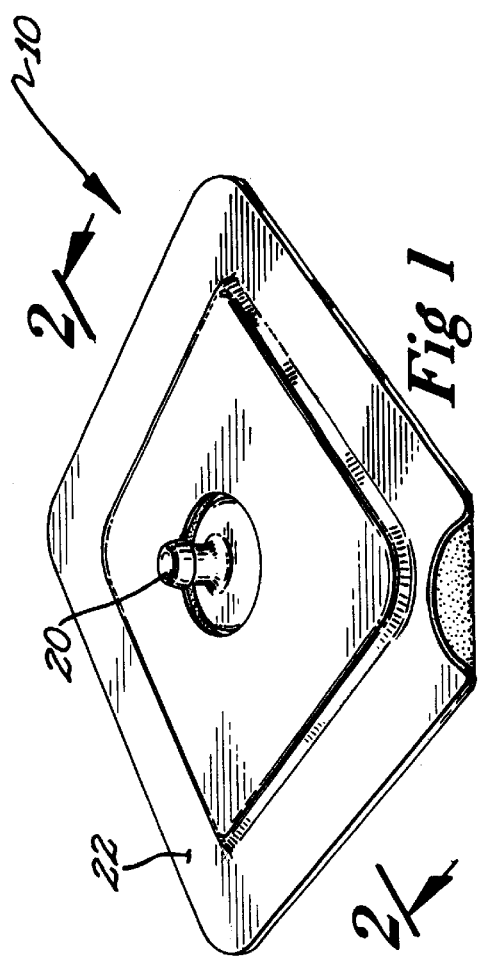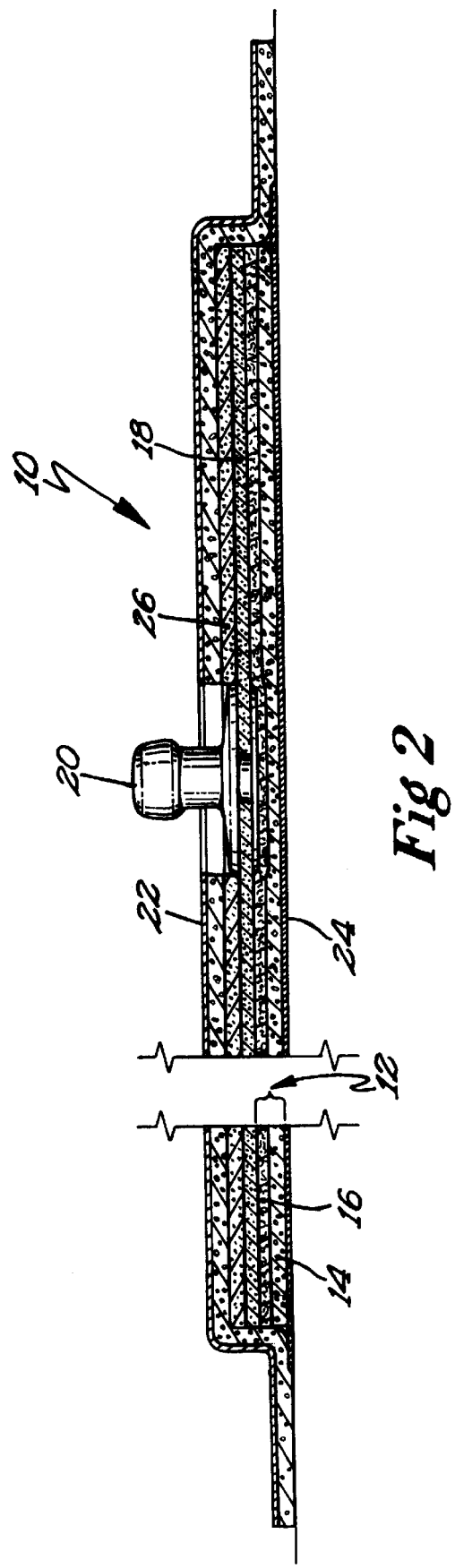

IONTOPHORESIS ELECTRODE

BACKGROUND OF THE INVENTION

This invention relates to an iontophoresis electrode for applying medicaments to the human body by applying electrical current in an effort to produce a desired reaction or effect. More specifically, the invention relates to an electrode that can be used in iontophoresis applications which is constructed of a polyvinyl chloride (PVC) or similar material and has a barrier layer to prevent plasticizer from migrating from the PVC or similar material into the conductive portion of the electrode.

Electrical current can be applied to the human body for many different purposes. For example, electrical current is commonly used in iontophoresis where drugs are delivered to the human body in a very controlled manner. In this application, the electrical current is applied to medicaments and they are delivered in a controlled manner to the human body in this manner. The level and duration of current supplied directly controls the amount of medication provided. Several controllers and systems exist for iontophoresis. The concept of iontophoresis is very well known to those skilled in the art.

As with any electrical system in which an electrical current is to be applied to the human body, the risk of electrical burns can exist. These electrical burns typically result from too much electrical charge being applied to the body—either through large amounts of current, or through prolonged application. It goes without saying that these burns need to be prevented, and close controls must be in place to insure that they do not occur. These controls include closely monitoring the systems that are being used, as well as monitoring all of the component. In this way, unexpected results can be prevented.

In order to have the electrical current applied to the desired drug reservoir, the electrodes preferably have a conductive layer which is attached to the current producing circuit. The conductive layer is configured to be adjacent the drug reservoir, and backed by some insulating material. One such configuration includes a foam backer with a carbon layer attached thereto. Also adjacent the carbon layer, opposite the foam backer, is the required drug reservoir. This carbon layer then provides the necessary conductivity to activate the drug delivery mechanisms.

In most iontophoresis systems, the electrodes are manufactured so as to be conformable to the body, while also having the desired electrical characteristics. In many medical applications, PVC films are used because of their softness and conformity. These films could work well in electrodes as the foam backing element because they would be capable of easily conforming to the body of the patient. Despite this potential advantage, PVC has a tendency to leach plasticizers into surrounding media. This is particularly problematic in the context of medical electrodes because this leaching can alter the electrical characteristics of the conductive materials. As can be appreciated, the uncontrolled change of an electrode's electrical characteristics can result in the undesired application of electrical current to the body, and possibly burns.

In the context of iontophoresis systems, changing the formulation of the material from which the backing layer was formed and/or crosslinking of the plasticizers with each other or the other components of the material and/or adhesive have been attempted without commercial success. Alternatively, the conductive layer of the electrode is constructed of material such as from foil, felt, or gauze formed of metal such as aluminum or stainless steel, which have little transference of plasticizers. However, because of increased burn risks, especially for metal conductive layers, electrodes of these types can only be used for short times.

Further, numerous other mechanisms have been attempted to control the characteristics of the electrodes. For example, U.S. Pat. No. 5,840,056 to Antanasoska provides an electrode having an incorporated pH buffer. This pH buffer is specifically configured to scavenge undesired H+ or OH−(hydrogen and hydroxide) ions created by the electrolysis of water. Similarly, U.S. Pat. No. 4,973,303 to Johnson et al. provides a buffered electrode in which a pH buffer is incorporated to again provide the scavenging function.

Another solution is provided in U.S. Pat. No. 4,886,489 where a flushing type action is used. In this system, a flushing compound is circulated through the electrode. In use, all undesired ions have been swept away in the circulating compound.

Another way to control the electrical current being applied to the patient is through control of the electrical supply circuit. It is recognized that many different type of circuits could be configured to provide the desired electrical signals. One such system which could be used for producing the necessary signals is described in U.S. Pat. No. 5,431,625 entitled Iontophoresis Electronic Device Having Ramped Output Current. U.S. Pat. No. 5,431,625 provides much more detailed description of such a circuit, and is herein incorporated by reference.

SUMMARY OF THE INVENTION

The present invention provides a solution to the plasticizer leaching problem by reconfiguring the electrode design. In the electrode configuration of the most preferred form of the present invention, a barrier layer is added between the foam backing layer and the carbon film conductive layer. This barrier layer is designed to prevent plasticizer migration that can occur from PVC or similar films having plasticizers forming the backing layer.

In one configuration, the barrier layer is designed as an impermeable layer of material such as polyethylene (PE), polyester, or any material in which the plasticizer is immiscible in. Such a barrier layer stops the migration of plasticizer and preserves the electrical conductivity of the conductive carbon layer.

In an alternative configuration, a sacrificial layer is utilized. This sacrificial layer will accept the migration of plasticizers, however will not effect the electrical characteristics of the electrode. For example, an additional layer of carbon could be incorporated which is isolated from the active carbon conductive layer. As such, leaching of plasticizers into this sacrificial carbon layer would not effect the conductivity of the active carbon conductive layer.

It is an object of the present invention to provide an electrode which utilizes PVC or similar material including plasticizers in its construction, however which also deals with the migration of plasticizers. As such, the use of material including plasticizers will not effect the electrical characteristics of the electrode.

It is another object of the present invention to include a barrier layer in an iontophoresis electrode which can actively deal with plasticizer leaching. This object is achieved by including a barrier layer which either prevents the migration of plasticizers or accepts this migration without alteration of the electrical characteristics of the electrode.

It is a further object of the present invention to provide a sacrificial layer of carbon along with an active conductive layer of carbon so that migration of plasticizers does not effect the electrical conductivity of the electrode.

It is yet another object of the present invention to provide an electrode which utilizes PVC and deals with the inherent plasticizer migration problem by including a barrier layer which prevents migration into the active electrode layer. As such, the active electrode layer will not change its electrical conductivity.

These and further objects and advantages of the present invention will become clearer in light of the following detailed description of an illustrative embodiment of this invention described in connection with the drawings.

BRIEF DESCRIPTION OF THE DRAWINGS

The illustrative embodiments may best be described by reference to the accompanying drawings where:

FIG. 1 shows a perspective view of an iontophoresis electrode according to the preferred teachings of the present invention; and FIG. 2 shows a cross-sectional view of the iontophoresis electrode of FIG. 1 according to section line 2—2 of FIG. 1.

All figures are drawn for ease of explanation of the basic teachings of the present invention only; the extensions of the Figures with respect to number, position, relationship, and dimensions of the parts to form the preferred embodiment will be explained or will be within the skill of the art after the following description has been read and understood. Further, the exact dimensions and dimensional proportions to conform to specific force, weight, strength, and similar requirements will likewise be within the skill of the art after the following description has been read and understood.

Where used in the various figures of the drawings, the same numerals designate the same or similar parts. Furthermore, when the terms "thickness," "over," "inwardly," "underside," and similar terms are used herein, it should be understood that these terms have reference only to the structure shown in the drawings as it would appear to a person viewing the drawings and are utilized only to facilitate describing the preferred embodiment.

DETAILED DESCRIPTION OF PREFERRED EMBODIMENTS

An iontophoresis electrode according to the preferred teachings of the present invention is shown in the drawings and generally designated 10. Generally, electrode 10 includes a drug reservoir 12 shown in its most preferred form of a bi-layer design. Particularly, reservoir 12 includes a medicament containing layer 14 and a buffer layer 16. Layer 14 in the most preferred form is formed of a hydrophilic foam but can be formed of any conductive polymer or similar material impregnated with an aqueous medicament solution or a porous material containing an electrolyte solution. In the preferred form, layer 14 has a thickness in the order of 0.080 inch with a tolerance of plus or minus 0.01 inch. Buffer layer 16, of the same size as layer 14 and containing immobilized buffer molecules, will scavenge H+ ions or OH– ions. In the most preferred form, layer 16 is a woven fabric, such as a cotton flannel, coated with an ion-exchange resin. In the preferred form, the fabric of layer 16 is purchased by areal weight in the order of 2.90 pounds per yard. The bi-layer reservoir 12 of the most preferred form is believed to be advantageous in providing a more consistent structure for coating with the resin such that less buffered resin is required and better pH control is provided over the entire surface of electrode 10. Also, there is less absorption of the medicament into the buffering resin in layer 16 resulting in lesser medicament fill requirements in layer 14 and greater drug delivery. Furthermore, a bi-layer reservoir 12 according to the teachings of the present invention also reduces the partitioning effect within the buffering resin. However, reservoir 12 could be constructed in other manners according to the preferred teachings of the present invention.

Reservoir 12 is positioned adjacent to a conductive layer 18 which in the most preferred form is a carbon film, but other conductive polymers could be used. Layer 18 is adapted to be attachable to an electrical power source, and in the most preferred form, suitable provisions 20 are provided to couple layer 18 to the electrical power source such as a DC generator, with provisions 20 being shown as a snap terminal in the most preferred form. Conductive layer 18 in the preferred form has a thickness in the order of 0.004 inch with a tolerance of plus or minus 0.002 inch. Layer 18 in the preferred form shown has a size corresponding to reservoir 12 and layers 14 and 16.

An adhesive covering or backing layer 22 is placed over conductive layer 18 to provide structural support for electrode 10 and adherence to the skin. Backing layer 22 in the preferred form has a thickness in the order of 0.027 inch with a tolerance of plus or minus 0.003 inch. Backing layer 22 can have a variety of shapes and is of a size considerably larger than layers 14 16, and 18, with layers 14, 16 and 18 being spaced inwardly from the periphery of backing layer 22. In the preferred form, backing layer 22 is formed of a film including plasticizers providing stretchability, softness and conformability and in the most preferred form is a PVC tape. However, backing layer 22 could be formed from a polyester film, a polyurethane film, a polyethylene film, a polyester elastomer, a polyurethane elastomer, or a polyethylene elastomer.

Layers 14, 16, and 18 are suitably held or attached in juxtaposed position against the underside of backing layer 22. In the most preferred form, electrode 10 includes a wicking paper layer 24 of a size larger than layers 14, 16, and 18 but smaller than layer 22. Layer 24 is held by adhesive of backing layer 22 in the preferred form. Layer 24 has a nominal thickness in the order of 0.005 inch in the most preferred form.

It can then be appreciated that plasticizers leach into surrounding media and specifically when backing layer 22 is formed of film including plasticizers, such plasticizers will migrate into conductive layer 18 and alter the electrical characteristics of conductive layer 18. Specifically, the presence of plasticizers in conductive layer 18 changes the resistivity of the conductive carbon element resulting in increased resistance to the extent that electrode 10 can shut down or result in the occurrence of electrical burns. In particular, in aging tests, the resistance of a carbon conductive layer 18 on the average was in the low 200's at time zero, was 5,016 ohms at 3 months, and 12,800 ohms at 9 months. Resistance of approximately 400 ohms or less is considered acceptable for iontophoresis medicament delivery. Due to the change of resistance, tunneling of current through reservoir 12 occurs resulting in uneven drug delivery and can result in pH buffering failures in the nonuniform areas. Time to failure for conventional electrodes, i.e. when the resistance of conductive layer 18 increased about 175% can be in as little as 40 minutes, with an average of 126.3 minutes until failure occurs. Electrode 10 according to the teachings of the present invention includes a barrier layer 26 interposed between backing layer 22 and conductive layer 18 and which acts as a diffusional boundary between backing layer 22 and conductive layer 18, with barrier layer 26 being of a size corresponding to layers 14, 16 and 18. In the most preferred form, barrier layer 26 has a flexibility corresponding to that of backing layer 22 so as not to detract from the advantages for which the material was chosen from which backing layer 22 is formed.

In a first preferred form of the present invention, barrier layer 26 is a sacrificial layer which accepts the migration of plasticizers from backing layer 22, with the plasticizers tending to remain in barrier layer 26 and not migrating therefrom into conductive layer 18. In a preferred form, barrier layer 26 is of an identical construction as conductive layer 18 and in the most preferred form is formed of carbon. In aging tests, the resistance of carbon barrier layer 26 and conductive layer 18 on the average was 261.1 and 244.6 ohms at time zero, respectively, was 20,300 and 275.1 ohms at six months, respectively, and 41,400 and 356.8 ohms at twelve months respectively.

It should be appreciated that the resistance of barrier layer 26 increases rapidly as layer 26 absorbs most of the migration of plasticizers to levels which are clearly unacceptable for iontophoresis medicament delivery whereas the migration of plasticizers is substantially stopped to conductive layer 18 so that its electrical resistance remains in acceptable limits for iontophoresis medicament delivery. It should then be appreciated that a single layer of twice the thickness will not have the same results as the plasticizers will migrate through the entire thickness. The air gap and break in continuity created by the use of the two layers act as a diffusional boundary to stop the plasticizers from leaching from barrier layer 26 into conductive layer 18. In fact, there are areas in conductive layer 18 in direct contact with barrier layer 26 which will have higher resistance as evidenced by dark spots in conductive layer 18. Forming barrier layer 26 of identical construction as conductive layer 18 is advantageous in inventorying components and quantity discount pricing.

In another preferred form, barrier layer 26 is formed of an impermeable material in which the plasticizer of layer 22 is immiscible in and stops the migration of the plasticizer into electrode 10 and thereby preserves the electrical conductivity of conductive layer 18. As an example, in aging tests, where barrier layer 26 is a 0.003 inch film of PE, the average resistance of a carbon conductive layer 18 was 241.5 ohms at time zero, was 368.4 ohms at six months, and 410.2 ohms at twelve months. Similarly, where barrier layer 26 is a 0.0064 inch film of PE, the average resistance of a carbon conductive layer 18 was 221.9 ohms at time zero, was 295.25 ohms at six months and was 341.8 ohms at twelve months. Similarly, where barrier layer 26 is a 0.003 inch polyester packing tape, the average resistance of a carbon conductive layer 18 was 237.3 ohms at time zero, 382.5 ohms at six months, and 442.4 ohms at twelve months.

Barrier layer 26 can be composed of PE, polyester, polyurethane, polypropylene, or similar material to which the plasticizers of backing layer 22 are immiscible or combinations thereof. Forming barrier layer 26 of the impermeable type according to the teachings of the present invention is generally less expensive as PE, polyester, polyurethane, polypropylene, and similar materials are less costly than carbon or electrically conductive polymers.

Barrier layer 26 should have a thickness which is able to function as a diffusional boundary to substantially prevent the migration of plasticizers into conductive layer 18 but which is not bulky to detrimentally affect the overall size of electrode 10. In the preferred form, barrier layer 26 can have a thickness which does not detract from the flexibility of backing layer 22 and in the preferred form which is between 0.001 and 0.01 inch. Layers 26 having a thickness of 0.001 inch or less are difficult to work with on manufacturing equipment whereas thickness of 0.01 inch or more tend to be too stiff, especially when barrier layer 26 is formed of polyester.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described in detail therein. Rather, reference should be made to the appended claims as indicative of the scope and content of the present invention.

What is claimed is:

1. A iontophoresis electrode for use in applying medicaments to the human body, comprising, in combination:

a conductive layer having electrical characteristics and adapted to be attachable to an electrical power source;

a barrier layer juxtaposed to the conductive layer;

a backing layer juxtaposed with the barrier layer on a side opposite the conductive layer, with the backing layer being fabricated from a material including plasticizers providing softness and conformability, with the conductive layer being formed of material into which the plasticizers can migrate altering the electrical characteristics; and a drug reservoir juxtaposed with the conductive layer on a side opposite the barrier layer, wherein the barrier layer prevents the undesired migration of plasticizers from the backing layer into the conductive layer, thus maintaining the electrical characteristics of the conductive layer.

2. The iontophoresis electrode of claim 1 wherein the barrier layer is an impermeable material so as to prevent the migration of plasticizers into the conductive layer.

3. The iontophoresis electrode of claim 2 wherein the barrier layer has a thickness of between 0.001 and 0.010 inches.

4. The iontophoresis electrode of claim 2 wherein the barrier layer has similar flexibility as the backing layer.

5. The iontophoresis electrode of claim 2 wherein the conductive layer is formed of carbon; and wherein the backing layer is formed of PVC.

6. The iontophoresis electrode of claim 5 wherein the barrier layer is formed of PE.

7. The iontophoresis electrode of claim 5 wherein the barrier layer is formed of polyester.

8. The iontophoresis electrode of claim 1 wherein the barrier layer is a sacrificial layer which is isolated from the conductive layer and accepts the migration of plasticizers.

9. The iontophoresis electrode of claim 8 wherein the barrier layer is identical to the conductive layer.

10. The iontophoresis electrode of claim 9 wherein the conductive layer is formed of carbon.

11. The iontophoresis electrode of claim 10 wherein the backing layer is formed of PVC.

12. The iontophoresis electrode of claim 8 wherein the backing layer is formed of PVC.

13. The iontophoresis electrode of claim 8 wherein the barrier layer has a thickness of between 0.001 and 0.010 inches.

14. The iontophoresis electrode of claim 8 wherein the barrier layer has similar flexibility as the backing layer.

15. The iontophoresis electrode of claim 8 wherein the backing layer is formed from a polyester film.

16. The iontophoresis electrode of claim 8 wherein the backing layer is formed from a polyurethane film.

17. The iontophoresis electrode of claim 8 wherein the backing layer is formed from a polyethylene film.

18. The iontophoresis electrode of claim 8 wherein the backing layer is formed from a polyester elastomer.

19. The iontophoresis electrode of claim 8 wherein the backing layer is formed from a polyurethane elastomer.

20. The iontophoresis electrode of claim 8 wherein the backing layer is formed from a polyethylene elastomer.

* * * * *